(12) United States Patent
Kuenen et al.

(10) Patent No.: US 11,540,757 B2
(45) Date of Patent: Jan. 3, 2023

(54) ASSESSING THE FUNCTIONAL ABILITY OF A PERSON TO PERFORM A TASK

(71) Applicant: KONINKLIJKE PHILIPS N.V., Eindhoven (NL)

(72) Inventors: Maarten Petrus Joseph Kuenen, Veldhoven (NL); Murtaza Bulut, Eindhoven (NL); Charles Frederik Sio, Eindhoven (NL); Ronaldus Maria Aarts, Geldrop (NL); Chaitanya Dongre, Vaals (NL)

(73) Assignee: Koninklijke Philips N.V., Eindhoven (NL)

( * ) Notice: Subject to any disclaimer, the term of this patent is extended or adjusted under 35 U.S.C. 154(b) by 973 days.

(21) Appl. No.: 16/304,890

(22) PCT Filed: Jun. 13, 2017

(86) PCT No.: PCT/EP2017/064355
§ 371 (c)(1),
(2) Date: Nov. 27, 2018

(87) PCT Pub. No.: WO2017/216137
PCT Pub. Date: Dec. 21, 2017

(65) Prior Publication Data
US 2020/0327989 A1    Oct. 15, 2020

(30) Foreign Application Priority Data

Jun. 13, 2016    (EP) ..................................... 16174094

(51) Int. Cl.
*A61B 5/16*    (2006.01)
*G16H 20/30*    (2018.01)
(Continued)

(52) U.S. Cl.
CPC .............. *A61B 5/16* (2013.01); *A61B 5/1113* (2013.01); *A61B 5/48* (2013.01); *A61B 5/6802* (2013.01);
(Continued)

(58) Field of Classification Search
None
See application file for complete search history.

(56) References Cited

U.S. PATENT DOCUMENTS

2004/0147817 A1    7/2004  Dewing et al.
2009/0155754 A1    6/2009  Shankle et al.
(Continued)

OTHER PUBLICATIONS

Southard, et al., "The Multiple Tasks Test as a predictor of falls in older adults", Science Direct, Gait & Posture, Elsevier, Amsterdam, NL, vol. 22, No. 4, Dec. 1, 2005, pp. 351-355.
(Continued)

*Primary Examiner* — G Steven Vanni

(57) ABSTRACT

Presented is a system and method for assessing the functional ability of a person to perform a task. The system comprises: a task identification unit adapted to identify the task to be performed by the person; and a task complexity unit adapted to obtain a task-specific complexity signal representative of a required level of functional ability to perform the identified task. A functional ability unit is adapted to obtain a functional ability signal representative of a determined functional ability of the person. An assessment unit is adapted to determine an ability of the person to perform the identified task based on the task-specific complexity signal and the functional ability signal.

12 Claims, 4 Drawing Sheets

(51) Int. Cl.
  *G16H 50/30*  (2018.01)
  *G16H 50/70*  (2018.01)
  *G16H 50/20*  (2018.01)
  *G16H 20/70*  (2018.01)
  *G16H 80/00*  (2018.01)
  *A61B 5/11*  (2006.01)
  *A61B 5/00*  (2006.01)
  *G16H 40/67*  (2018.01)

(52) U.S. Cl.
  CPC ............ *G16H 20/30* (2018.01); *G16H 20/70* (2018.01); *G16H 50/20* (2018.01); *G16H 50/30* (2018.01); *G16H 50/70* (2018.01); *G16H 80/00* (2018.01); *A61B 2505/07* (2013.01); *G16H 40/67* (2018.01)

(56) References Cited

U.S. PATENT DOCUMENTS

| | | |
|---|---|---|
| 2014/0007009 A1 | 1/2014 | Kulusky, Jr. et al. |
| 2014/0067730 A1 | 3/2014 | Kozloski et al. |
| 2014/0164945 A1 | 6/2014 | Junqua et al. |
| 2014/0276130 A1 | 9/2014 | Mirelman et al. |

OTHER PUBLICATIONS

Fried, et al., "Physical Disability in Older Adults: A Physiological Approach", Journal of Clinical Epidemiology, Pergamon, GB, vol. 47, No. 7, Jul. 1, 1994, pp. 747-760.

ASSESSING THE FUNCTIONAL ABILITY OF A PERSON TO PERFORM A TASK

This application is the U.S. National Phase application under 35 U.S.C. § 371 of International Application No. PCT/EP2017/064355, filed on Jun. 13, 2017, which claims the benefit of European Application Serial No. 16174094.9, filed Jun. 13, 2016. These applications are hereby incorporated by reference herein.

FIELD OF THE INVENTION

This invention relates to a system and method for assessing the functional ability of a person to perform a task.

BACKGROUND OF THE INVENTION

Assessment or monitoring of a person's functional abilities (such as cognitive and/or physical abilities) is of primary concern in many branches of medicine, including geriatrics, rehabilitation and physical therapy, neurology and orthopedics, nursing and elder care.

Investigations have found that an individual's functional ability can actually be environment-specific, since function increases when subjects are in familiar surroundings due to reduced confusion. Also, one-time assessment of functional ability does not allow for assessment of variability of functional performance over the course of a day or several days, nor does it allow for assessment of change which is important in determining the adequacy of certain clinical services, care and treatments following functional reduction or loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they are living independently in their own home or within familiar surroundings. For example, one such known system for detecting activities of daily living of a person system comprises three main components: (i) a sensor system that collects information about the person's activities and behaviors; (ii) an intelligence (or information processing) system that interprets the sensor signals for the care needed; and (iii) a user interface system that enables care givers to inspect the interpreted (processed) information. The intelligence system typically makes use of computational techniques known in the art as artificial intelligence.

SUMMARY OF THE INVENTION

However, such conventional devices/systems do not provide adequate assessment and monitoring of functional ability and so, typically, assessment and monitoring of functional ability is done through costly face-to-face consultations with a medical professional or caregiver. Thus, any advantages gained due to increased independence or empowerment of a person are largely negated by the time and resource requirements associated with regular consultations.

There is thus a need for an improved device/system. This need is at least partially fulfilled with the invention as defined in the independent claims. The dependent claims provide advantageous embodiments.

According to a first aspect of the invention, there is provided a system for assessing the functional ability of a person to perform a task, the system comprising: a task identification unit adapted to identify the task to be performed by the person; a task complexity unit adapted to obtain a task-specific complexity signal representative of a required level of functional ability to perform the identified task; a functional ability unit adapted to obtain a functional ability signal representative of a determined functional ability of the person; and an assessment unit adapted to determine an ability of the person to perform the identified task based on the task-specific complexity signal and the functional ability signal, and to generate an assessment signal representative of the determined ability of the person to perform the identified task.

The assessment signal may indicate the need for a caregiver to assist the person in performing the identified task. Thus, there is proposed a concept for reducing the burden on caregivers and for improving the person's (e.g. the patient's) feeling of self-empowerment or independence, while maintaining a required level of care and safety.

The invention is based on the insight that a system for assessing the cognitive and/or physical ability of a person to perform a task can be used to generate a signal for an alerting or warning system which can indicate a person is in need of help, for example. It is proposed to generate such a signal based on two types of information. The first type of information may relate to task-specific information that is representative of a required level of functional ability to perform a specific task (e.g. an identified task), and the second type of information may relate to functional ability information that is representative of a functional ability of a person seeking to perform the task. In other words, an assessment signal may be generated based on information about the complexity of a task, wherein the task has been inferred or detected (by a task identification system) from one or more sensor signals, and further based on person-specific information about a functional ability of a person seeking to perform the task.

Thus, a detected or inferred task may be provided as an input to an assessment unit, along with information relating to a functional ability of the person (e.g. a cognitive ability and/or a physical ability of the person), and the assessment unit may generate an assessment signal dependent on the input information. In this way, the assessment unit may determine an ability of a specific person to perform a particular task so as to enable the creation of personalized information (such as warnings, guidance, and alerts). Highly specific and/or accurate warnings, guidance and alerts may therefore be generated that are unique to characteristics of the task and/or the monitored person/individual.

Furthermore, the monitor unit may combine the raw sensor data/signals with determined assessments, thus providing a hybrid form of alert.

There is proposed a system which (i) identifies a task to be performed by a person; (ii) measures or determines a functional skill level (e.g. cognitive ability and/or physical ability) of the person; (iii) compares the measured/determined skill level of the person with a minimum skill level required to perform the identified task (e.g. from a lookup table of required level per task or set of tasks); and determines a need for guidance based on the result of the comparison. Further, the minimum skill level required may be updated based on an evolution of measured skill levels for tasks (e.g. using a feedback loop for learning per person).

Embodiments may therefore employ the idea of recognizing clusters of daily life tasks (e.g. ADLs), like making coffee, and then estimating the persons' ability to perform the task(s). Measuring or determining a functional skill level can be done using observation of various values or characteristics of a person, such as: repetitive motion (related to being confused), speech, facial expression, stress and anxiety (via heart rate and/or galvanic skin response), levels of physical activity in the past hours/days, success in similar tasks in a predetermined period of time preceding the current task, etc.

A functional skill level required to perform a task can be based on several factors such as:
 (i) the complexity of performing the task (e.g. preparing a cup of coffee is more difficult than preparing a glass of water);
 (ii) the safety risk associated with the device/items used specific task (e.g. using the oven carries more safety hazards than brushing one's teeth);
 (iii) the safety risk associated with the results of a task (e.g. a wrongly prepared foodstuff carries more safety hazards than a wrongly vacuumed floor);
 (iv) leaving the house in general (or in more detail without appropriate clothing, keys etc.);
 (v) entering a car at the driver's position;
 (vi) safely preparing food that needs use of sharp knives to cut or boiling water/soup as opposed to preparing sandwiches;
 (vii) operating heating system during winter;
 (viii) operating hot/cold water combinations in the shower (risk of hypothermia or burning skin with too hot water);
 (ix) not forgetting metallic objects or enclosed foods (e.g. egg, melon, etc.) in the microwave oven;
 (x) an amount of physical strength, exertion or movement required to perform the task; and
 (xi) a level of physical mobility required of a person to perform the task.

By way of example, proposed embodiments may determine a minimum level of supervision required by a caregiver to allow the person (e.g. patient) to perform the identified task, and can then alert the caregiver if his/her supervision is required. This may help to maximize the use of a patient's functional abilities and have a positive effect on his/her self-empowerment. It will also help to minimize the amount of supervision and burden of care required from the caregiver, while maintaining adequate levels of safety.

It is also proposed to consider a known or perceived risk associated with a certain activity or task. Such risks may be derived from characteristics of the activity or task (such as difficulty, equipment used, potential hazards, result of failure, etc.) and from the functional ability of the person.

Accordingly, in an embodiment, the system may further comprise a risk analysis unit adapted to obtain a task-specific risk signal representative of a risk of the identified task. The assessment unit may then be adapted to determine an ability of the person to perform the identified task further based on the task-specific risk signal. By way of example, the task-specific risk signal may comprise information relating to at least one of:
 the person's perceived risk of the identified task; a caregiver's perceived risk of the identified task; and an availability of the caregiver.

It is noted that a risk associated with a task may be perceived differently by different persons. Put another way, a level of risk may be subjective and thus vary according to the perceptions of an individual. For example, the perceived risk of a certain activity as observed by the patient may be very different from the perceived risk as observed by a medical professional or caregiver.

Thus, proposed embodiments may take account of the risk(s) perceived by both patient and caregiver as important factors for the purpose of determining an overall (e.g. objective, summary, or composite) risk of a task. For example, if the caregiver does not feel confident about the patient performing a certain activity, the system may be adapted to determine that the patient is simply not able (or permitted) to perform the task. Embodiments may therefore take account of:
 (i) a perceived risk of a certain activity as observed by the patient; and
 (ii) the risk of an activity as perceived by the caregiver.

Preferably, the perceived risk of the task as observed by both the patient and the caregiver are accounted for in the task specific risk signal.

Assessment of the risk as perceived by patient and caregiver may preferably involve monitoring of both patient/person and caregiver. For example, the perceived risk of a task as observed by the patient may be derived or inferred from stress levels observed in the patient while preparing for the task, and/or from previously observed correlations between task characteristics and stress levels of the patient. Alternatively, or additionally, the perceived risk of a task as observed by the patient may be derived from previous outcomes of performing the same task (e.g. whether or not an accident occurred when previously performing the same task). Likewise, the perceived risk of a task as observed by a caregiver may be derived or inferred by correlating the state of the caregiver when activities are performed by the patient (e.g. whether or not the caregiver assisted the patient in performing a specific task or intervened, or stress levels observed in the caregiver in previous occurrences or while the patient is preparing for the task). Preferred embodiments may therefore be adapted to monitor both the caregiver and the patient and to provide an output signal to both caregiver and the patient.

Multiple caregivers may have a different perception of the risk associated with a task. For this reason, embodiments may provide a different assessment for different caregivers. Also, information may be shared between different caregivers, so that a refined or optimal perception of risk for the patient may be employed. This may also be provided as feedback to caregivers, allowing them to refine their supervision activities.

Further, the risk analysis unit may be adapted to receive a sensor signal representative of a detected value of a property of at least one of: the person; and the environment, and to determine the risk of the identified task based on the received sensor signal.

Embodiments may also enable some of the processing load to be distributed throughout the system. For example, pre-processing may be undertaken at a sensor so that primitive task identification or inference may be implemented at the sensor(s). Alternatively, or additionally, processing could be undertaken at a communication gateway. In some embodiments, processing may be undertaken at a remote gateway or sever, thus relinquishing processing requirements from an end-user or output device. To enable users to modify parameters or information used for assessment, editing of environmental information or perceived risks may be hosted in the monitored environment (e.g. house), whereas editing of assessment algorithms may be done remotely at a central server. Such distribution of processing and/or hardware may allow for improved maintenance abilities (e.g. by centralizing complex or expensive hardware in a preferred location). It may also enable computational load and/or traffic to be designed or located within a networked system according to the processing capabilities available. A preferable approach may be to process sensor data locally and transmit extracted events (for example, open/close from accelerometer data) for full processing at a remote server.

Further, alerts or warnings may be generated based on the occurrence of such user-defined tasks or risks. It may also enable only part of the inference system/approach to employ signal processing, thus reducing processing requirements while also enabling the inference of a functional ability to perform a task.

The task identification unit may be adapted to receive a sensor signal representative of a detected value of a property of at least one of: the person; and the environment, and to identify the task to be performed by the person based on the received sensor signal.

Similarly, the functional ability unit may be adapted to receive a sensor signal representative of a detected value of a property of at least one of: the person; and the environment, and to determine the functional ability of the person based on the received sensor signal.

By way of example, embodiments may further comprise a sensor adapted to detect a value of a property of at least one of: the person; and the environment; and to generate the sensor signal representative of the detected value.

There exist many sensors that can be employed by embodiments. Typical sensors include PIR (Passive Infra Red; measure movement and presence), OC (open-close; measure state of doors, in particular front doors, windows, and cupboards, including refrigerators), power sensors (measure current consumption of appliances, such as microwave, water cookers, TV, etc.), and pressure mats (measure occupancy of user sitting in chair, lying in bed, standing on door mat in front of front door, etc.). Many others exist and are conceivable, such as sensors to signal light switch state, or sensors that measure environmental conditions such as humidity, CO2 level (or CO and smoke), etc. A further range of sensors are those based on physical quantities, such as accelerometers, magnetometers, gyroscopes, and air pressure sensors. Accelerometers, for example, can also measure state of doors and their open-close movements. Yet another range of sensors consists of microphones and cameras (including infra-red (IR), or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in the environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof.

The sensors may also be adapted to undertake primary processing of the detected values, such a signal filtering, sampling, conditioning, etc., so as to reduce a required transmission bandwidth and/or transmission duration for example.

Non-intrusive monitoring may therefore be realized with relative simple sensors that provide data on specific ambient conditions or properties/parameters of the environment (such as temperature or humidity for example), or properties of the person (such as movement, for example). Such sensors for measuring ambient condition or properties/parameters of the environment may be simple, small and/or cheap. Also, the movement of the person may be detected with, for example, a Passive InfraRed (PIR) sensor which is a cheap component. Movement sensors may be used to switch on lighting and people are therefore typically familiar with their usage. Thus, embodiment may employ sensors that are considered to be non-intrusive and more easily accepted by the monitored person. Yet, with the data provided by these sensors, a task may be identified and/or provide information useful for determining an ability of the person to perform an identified task.

For example, with a humidity sensor and a movement sensor in the bathroom it may be inferred that the person is about to take a shower. In a further example, with a temperature sensor and a movement sensor in the kitchen it may be determined that the person is going to prepare a hot meal. It is a further advantage that the sensors may be stationary sensors that are located for example in the bathroom and in the kitchen, thus making it unnecessary for the person to wear a device.

Activities of daily living concern basic activities that a person executes on a regular basis. Examples of activities of daily living are eating; cooking; medicating; sleeping; toileting; bathing; washing, etc. Embodiments may thus determine an ability of a person to perform ADLs in a non-intrusive manner.

Embodiments may further comprise a user input interface adapted to receive user inputs for defining or modifying one or more pieces of information that may be used for the purpose of assessing a person's functional ability to perform a task. This may reduce computational complexity and may also enable a user of the system (such as the care giver or medical practitioner, for example) to create, define, modify, and/or alter rules, parameters and constraints. Embodiments may therefore enable signals or information to be defined, modified, and extended by a user, thereby providing the flexibility to the many different contexts in which the system operates.

In an embodiment, the system may further comprise a user input interface adapted to receive a user input for defining or modifying one or more alert conditions, and the assessment unit may then be adapted to generate the assessment signal further dependent on the one or more alert conditions.

In a further embodiment the assessment unit may be adapted to generate the assessment signal based on a comparison of the functional ability signal with a predetermined threshold. For example, this provides the advantage that for example an alarm may be given if the person's functional ability is below a minimum level indicating that for example the person's functional ability is impaired or has deteriorated.

Embodiments may further comprise a task complexity data store adapted to store data relating to factors that influence required levels of functional ability to perform tasks. The task complexity unit may then be adapted to access data stored the task complexity data store and to obtain the task-specific complexity signal based on the accessed data.

Embodiments may be further adapted to store the determined ability and/or tasks/activities of the person in a database. Thus, the pattern(s) of ability of the person may be stored. Shifts in this pattern may indicate that the person is in need of help.

The stored abilities and/or activities of the person may form a pattern that characterizes said person. Deviations in the monitored abilities or tasks of the person may be used as an indicator of the well-being of the person. For example, elderly people that suffering a reduction in functional ability will typically exhibit one or more shifts in their behavioral pattern. They will start to forget to take a shower and lose the feeling of time. Therefore, in a further embodiment, the database may be analyzed for irregularities or shifts in patterns. An irregularity in the database may be detected, and an alert signal generated in response to the detected irregularity.

In a further embodiment, the assessment unit may be further adapted to detect an irregularity in the database. For example, by adding time information to the measured a property of the environment (such as an ambient condition like humidity or temperature), the time spent between the activities may be determined. With the time information, the frequency of the activity may be determined. For example, the frequency of the determined activity 'preparing a hot meal' may be 'once a day', or '5 times a week'. An irregularity in the activity database may then, for example, be that the time spent between the determined activities of 'preparing a hot meal' has increased. For example the average time spent may be determined using the data from the activity profile. When the time spent between two successive determined activities of 'preparing a hot meal' is larger than for example 1.5 times the average time spent this indicates an irregularity.

In a further embodiment the monitor unit may be further arranged to generate an alert signal in response to a detected irregularity. The irregularity may indicate that the person is in need of help. In a further example, a medical practitioner, a caregiver, a family member or close relative may be advised by the system (using the alert signal) to pay a visit to the person.

In a further embodiment the monitor signal may be given to the person himself/herself. For example, the warning signal may be a feedback signal advising the person to take a certain medication or preventative measures/action.

In some embodiments, the assessment unit may be adapted to determine an ability of the person to perform the identified task further based on historical information relating to one or more previously determined representations the person's functional ability. By using historical information, the accuracy and personalization of assessments may be improved.

Embodiments may further comprise an input interface adapted to receive an input for defining or modifying at least one of: the task to be performed by the person; the required level of functional ability to perform the identified task; the functional ability of the person; the risk of the identified task; and data relating to factors that influence required levels of functional ability to perform tasks.

Example of proposed systems may be adapted to provide the generated assessment signal to at least one of: the person; a medical practitioner; and a caregiver.

The invention further provides a method for assessing the functional ability of a person to perform a task, the system comprising: identifying the task to be performed by the person; obtaining a task-specific complexity signal representative of a required level of functional ability to perform the identified task; obtaining a functional ability signal representative of a determined functional ability of the person; determining an ability of the person to perform the identified task based on the task-specific complexity signal and the functional ability signal; and generating an assessment signal representative of the determined ability of the person to perform the identified task.

Proposed methods may also take account of a known or perceived risk associated with the identified task. Such risks may be derived from characteristics of the activity or task and/or from the determined functional ability of the person.

Accordingly, in an embodiment, the method may further comprise obtaining a task-specific risk signal representative of a risk of the identified task. The step of determining an ability of the person to perform the identified task may then be further based on the task-specific risk signal. Also, the task-specific risk signal may comprise information relating to at least one of: the person's perceived risk of the identified task; a caregiver's perceived risk of the identified task; and an availability of the caregiver.

Thus, proposed embodiments may take account of the risk(s) perceived by both patient and caregiver as factors for the purpose of determining an overall (e.g. objective, summary, or composite) risk of a task. Embodiments may therefore take account of: (i) a perceived risk of a certain activity as observed by the patient; and (ii) the risk of an activity as perceived by the caregiver. The non-intrusive character of the assessment may be realized by measuring at least one property of the person and the environment, rather than by for example surveillance by camera of the person.

According to yet another aspect of the invention, there is provided a computer program product for assessing the functional ability of a person to perform a task, the computer program product comprising computer-readable program code downloadable from a communications network, or storable on, or stored on a computer-readable storage medium, which computer-readable program code, when run on a computer causes the computer to perform the steps of claims 12-14. The computer program product can be suitable to work with a server device and client device including system. Part of the steps can be performed on the server device while the other or another part of the steps is performed on the client device. The server and client device can be remote from each other and connected through wired or wireless communication as known in the art. Alternatively, all steps are performed on a server device or on a client device.

In an embodiment, a computer system or device may be provided which comprises: a computer program product according to an embodiment; and one or more processors adapted to perform a method according to an embodiment by execution of the computer-readable program code of said computer program product. The system or device can comprise a client device and server device, or either one of the two for execution of the method steps. The server and client device can have communication devices for communicating with each other using wired or wireless communication protocols.

In a further aspect the invention relates to a computer-readable non-transitory storage medium comprising instructions which, when executed by a processing device, execute the steps of the method of a method of assessing the functional ability of a person to perform a task according to an embodiment.

The computer program product can have code for communicating results of any of the method steps to a user. Such code can include code for generating imagery, video and/or audio output. The system, client and/or server device can include a display and/or audio output devices (such as speakers) for generating the output.

Proposed are concepts which, based on observations of everyday normal tasks, can estimate a person's functional status, impairment of it, and assess the person's ability to perform a task.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Figure 1:
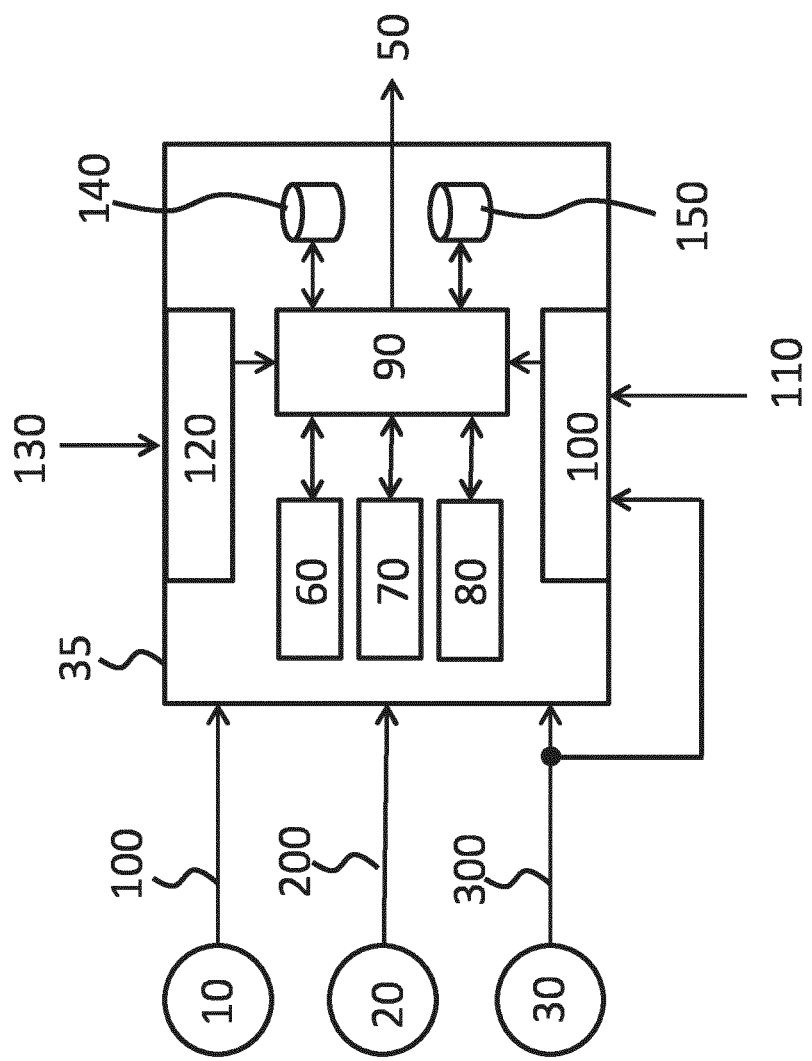
FIG. 1 is a simplified block diagram of a system for assessing the functional ability of a person to perform a task according to an embodiment.

Proposed is a concept for assessing the functional ability of a person to perform a task. Persons that may be monitored by embodiment may, for example, include a disabled person, an elderly person, an injured person, a medical patient, etc.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented. Also, it should be understood that reference to a functional ability of a person is intended to mean a cognitive ability of the person and/or a physical ability of the person. Thus, a functional ability of a person relates to the person's ability to perform activities of daily living (ADLs), and this in turn may depend on a cognitive ability of the person and/or a physical ability of the person. Cognitive (or mental) abilities are brain-based skills used to carry out a task, whereas physical abilities are physical skills or traits used to perform a physical act.

It has been recognized that in many care situations there is a need to be informed about the tasks or ADLs a person is performing. There may also be a need to be alerted when the functional ability of the person is such that they may be unable to perform the task or ADL without assistance. The task(s) or context can be different per case.

By way of example, ADLs may include:
  (i) Medication
    a. Is the elder taking his medicine in proper way at proper moments?
  (ii) Sleep
    a. Is the elder sleeping sufficiently and undisturbed?
  (iii) Eating/Drinking
    a. Is the elder eating sufficiently and regularly?
    b. Does he prepare meals by himself?
  (iv) Physical activity
    a. Is the elder active during the day?
    b. Is there little sedentary behavior?
  (v) Toileting
    a. Is the elder toileting in normal way?
    b. Are there frequent visits to the toilet during the night?
  (vi) Bathing
    a. Is the elder bathing adequately?
  (vii) Being In/Out House
    a. Is the elder going out?
  (xiii) Ambient climate
    a. Is the environment "clean"?
    b. E.g., is temperature proper, is the $CO_2$ level healthy?
  (ix) Etc.

Based on the above exemplary ADLs, the following examples warnings and alerts may be:
  A. Sign of activity, or sign of inactivity
  B. Presence in rooms considered risky (e.g. alone in kitchen when elder is suffering dementia)
  C. Leaving the house at unexpected moments, such as during the night
  D. Exceptional frequency or exceptional duration of toilet visits
  E. Exceptional duration of bathing
  F. Sleeping shorter
  G. Reduced activity Embodiments of the present invention are therefore directed toward enabling a functional ability of a person to be monitored and assessed in relation to performed tasks. This may be used to generate an alert signal for an alerting or warning system that can indicate the person is in need of help in order to complete a task, for example.

Embodiments are based on the insight that a system for monitoring ADLs of a person can be used to assess whether the person has the functional ability to perform a particular task. It is proposed to generate such an assessment based on information relating to an identified (e.g. detected) task and information relating to the person (e.g. physical characteristics, properties, behavioral trait, etc.) Some of this information may be inferred from a sensor output signals (in other words, an inferred task or value), whereas other information may relate to a sensor output signal itself. In other words, embodiments may be based on the concept that an assessment of a person's functional ability to perform a particular task a monitor may be made based on inferred information and/or based directly on one or more sensor signals. Inferred tasks may therefore be used a first input of an assessment unit, and raw sensor signals/data may be used as a second input of the assessment unit.

Also, proposed is a concept of basing the assessment on a risk-based formalism. Further, only a part of the assessment may use the risk-based formalism so as to reduce overall computational complexity. In particular, it has been realized that a risk associated with performing a task may be perceived differently by the person/patient and by a caregiver. A person's perceived risk of a task may be derived from pertinent information that only the person is aware of himself/herself. For example, a person may have the unique knowledge that the last time they performed a particular task (such as making a hot beverage, for example), significant difficulties were experienced (such as difficulty in lifting a full kettle of water) although the task was performed successfully (albeit slowly). Such information may not be known by a caregiver and/or detectable by sensors employed by the system, for example. Accordingly, taking account of a user's perceived risk may provide useful information for improving the accuracy or reliability of the assessment process.

Similarly, a caregiver's (or medical professional's) perceived risk of a task may be derived from pertinent information that only the caregiver (or medical professional) is aware of himself/herself. For example, a caregiver may have the unique knowledge that the last time the person performed a particular task (such as going to the shops, for example), significant difficulties were experienced (such as performed activities not matching observed intentions, for example) although the task was performed successfully (albeit slowly or in a confused manner). Such information may not be known by the assessed person and/or detectable by sensors employed by the system, for example. Accordingly, taking account of a caregiver's (or medical professional's) perceived risk may provide useful information for improving the accuracy or reliability of the assessment process.

It is also proposed to take account of a known or perceived risk associated with a certain activity or task when assessing whether or not the person should undertake a specific the identified task. The assessment process may therefore determine an ability of the person to perform at the identified task further based on a task-specific risk signal, wherein the task-specific risk signal comprises information relating to the person's perceived risk of the identified task and to the caregiver's perceived risk of the identified task. Thus, it is proposed to take account of the risk(s) perceived by both patient and caregiver for the purpose of determining an overall (e.g. objective, summary, or composite) risk of a task. In this way, proposed implementations may adapt to the specific circumstances, person, and available/present/ responsible caregiver so as to make a risk assessment which is tuned, for example, to the preferences of the person or caregiver. In this way, supervision of a person may be streamlined to requirements on a dynamic basis.

Embodiments thus propose the use of user-specific and task-specific information that may be obtained by and/or provided by an ADL monitoring system/method so that assessment of a person's functional ability to perform a task is tailored to the person and the task. Such a proposed assessment system/method may therefore be employed in a system for monitoring ADLs of a person within an environment.

FIG. 1 shows an embodiment of a system according to an embodiment of the invention comprising a plurality of sensors 10, 20, 30 arranged to measure a property of at least one of: the person; and the environment in which the person is.

Here, the first sensor 10 is a sensor that is adapted to detect a value of an ambient condition parameter of the environment, such as temperature or humidity for example. The second sensor 20 is a movement sensor 20 adapted to detect movement of the person that is monitored. The third sensor 30 is a power sensor 30 adapted to detect a value of the power consumption of an electrical appliance used by the person within the environment. The first 10, second 20 and third 30 sensors are adapted to output first 100, second 200 and third 300 sensor output signals, respectively, which are representative of the detected value(s).

The sensors 10,20,30 communicate their output signals 100,200,300 via wired or wireless connection. By way of example, the wireless connection may comprise a short-to-medium-range communication link. For the avoidance of doubt, short-to-medium-range communication link should be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), ISM Band, Near Field Communication (NFC), RFID, 6LoWPAN, UWB, Wireless HART, Wireless HD, Wireless USB, ZigBee. Examples of medium-range communication links include Wi-Fi, Z-Wave.

The system further comprises an signal processing unit 35 adapted to receive the first 100 to third 300 sensor output signals and to assess the functional ability of a person to perform a task based (at least in part) on the received sensor output signals. The signal processing unit 35 is adapted to generate an assessment output signal 50 representative of the determined ability of the person to perform the identified task.

The signal processing unit 35 also comprises a task identification unit 60 adapted to identify the task to be performed by the person. This, for example, may be done based on the first 100 to third 300 sensor output signals.

Further, the signal processing unit 35 comprises a task complexity unit 70 adapted to obtain a task-specific complexity signal representative of a required level of functional ability to perform the identified task. The signal processing unit 35 also comprises a functional ability unit 80 adapted to obtain a functional ability signal representative of a determined functional ability of the person.

Based on the task-specific complexity signal and the functional ability signal, an assessment unit 90 of the signal processing unit 35 determines an ability of the person to perform the identified task. The assessment unit 90 then generates the assessment signal 50 representative of the determined ability of the person to perform the identified task.

Accordingly, the assessment signal 50 provided as an output from basic processing unit 35 may indicate the need for a caregiver to assist the person in performing the identified task. Put another way, the assessment signal 50 is generated based on information about the complexity of a task (e.g. obtained by the task complexity unit 70), wherein the task has been inferred or detected (by the task identification unit 60) from one or more sensor output signals, and further based on person-specific information about a functional ability of a person seeking to perform the task (e.g. obtained by the functional ability unit 80).

It will therefore be understood that the embodiment of FIG. 1 is adapted to (i) identify a task to be performed by a person; (ii) measure or determine a functional skill level (e.g. functional ability) of the person; (iii) consider the measured/determined skill level with a functional ability required to perform the identified task (e.g. from a lookup table or database); and (iv) assess the functional ability of the person to perform the identified task. The system of FIG. 1 may thus determine a need for a person to receive guidance or help in order to perform a specific task.

Measuring or determining a functional skill level can be done using observations of various values or characteristics of a person as obtained by the sensors 10, 20, 30 for example. In this regard, many methods and approaches for determining instantaneous functional skill of a person have been extensively described in previous publications and are widely known to skilled persons in the fields of patient monitoring and ADL monitoring systems/method. Detailed description of determining a functional skill of a monitored person will therefore be committed. However, for completeness, it is noted that such known approaches to determining functional skill of a person may involve tracking of features related to repetitive motion, speech, facial expression, stress and anxiety (via heart rate and/or galvanic skin response for example), levels of physical activity during a predetermined period of time, success in similar tasks in a predetermined period of time preceding the current task, etc. Also, additional inputs useful for determining a functional skill level may be provided by additional, interconnected devices. For example, previous incorrect use of a device may be used to imply a lower functional skill score/level and vice versa.

Determining, by task complexity unit 70, a functional skill level required to perform a task can, by way of example, be based on several factors such as: predetermined values representing a complexity of the task (e.g. skill level numbers or complexity scores); safety risks associated with the task and/or device/items used in performing task; dependency on preceding tasks; and safety risks associated with the results of incorrectly or poorly performed task. Information about these factors may be stored in a local or remote database and accessed by the task complexity unit 70 for the purpose of determining a functional skill level required to perform the identified task. Thus, the task complexity calculation may be dynamic in that it can account for tasks having sub-tasks, which in turn may have sub-tasks, and complexity of the sub-tasks can depend how preceding sub-tasks were performed. Information about tasks and their sub-tasks and/or their interrelationship(s) or dependency with/on other tasks may thus be obtained (e.g. from a database) and employed for the purpose of task complexity.

The embodiment of FIG. 1 further comprises a risk analysis unit 100 that is adapted to obtain a task-specific risk signal representative of a risk of the identified task. Here, the task-specific risk signal comprises information relating to the: the person's perceived risk of the identified task; and a caregiver's perceived risk of the identified task; and an availability of the caregiver. The assessment unit 90 is adapted to determine an ability of the person to perform at the identified task by taking further account of the task-specific risk signal.

For the purpose of obtaining such information, the risk analysis unit 100 is adapted to receive (from the $3^{rd}$ sensor 30) a sensor signal 300 representative of a detected value of a property of at least one of: the person; and the environment. The risk analysis unit 100 is also adapted to receive a user input signal 110 comprising information relating to a user-perceived and/or a caregiver-perceived risk.

The risk analysis unit 100 therefore generates a signal which takes account of account of the risk(s) perceived by the person (e.g. patient) and/or caregiver as relevant for the purpose of determining an overall (e.g. objective, summary, or composite) risk of a task. A representation of the overall risk can then be provided by the risk analysis unit 100 to the assessment unit 90 for the purpose of determining whether a person has the functional ability to undertake a specific task (with or without assistance, for example). Thus, by way of example, if the caregiver inputs a signal indicating that a risk associated with the monitored person undertaking a certain activity exceeds an acceptable level, the assessment unit 90 may be adapted to determine that the patient is simply not able (or permitted) to perform the task. It will therefore be understood that the risk analysis unit 100 is adapted to account for:

(i) a perceived risk of a certain activity as observed by the patient—this can be derived from previously observed correlations between task characteristics and stress levels, or from previous outcomes (e.g.: if the user spoilt coffee over his hand the last time he was performing the task 'making coffee'); and (ii) the risk of an activity as perceived by the caregiver—this can be derived by correlating the caregiver state to the activities performed by the patient, and from the observed interventions by the caregiver during the same type of activities.

In the example of FIG. 1, assessment of the risk as perceived by patient and caregiver therefore involves monitoring of both the person (e.g. patient) and a caregiver.

The data processing unit 35 further comprises a user input interface 120 that is adapted to receive (e.g. user) inputs for defining or modifying information that may be used for the purpose of assessing a person's functional ability to perform a task. By way of example, the user input interface 120 of FIG. 1 is adapted to receive user inputs for defining or modifying at least one of: the task to be performed by the person; the required level of functional ability to perform the identified task; the functional ability of the person; the risk of the identified task; and data relating to factors that influence required levels of functional ability to perform tasks.

This may reduce computational complexity and may also enable a user of the system (such as the care giver or medical practitioner, for example) to create, define, modify, and/or alter rules, parameters and constraints. Embodiments may therefore enable signals or information to be defined, modified, and extended by a user, thereby providing the flexibility to the many different contexts in which the system operates.

In this embodiment, the user interface 120 is adapted to receive user inputs 130 for defining or modifying: one or more task inference rules, instructions or conditions; one or more functional ability rules, instructions or conditions; and one or more alert conditions. Based on such user inputs, the user interface 120 provides information to the assessment unit 90, and the assessment unit 90 then determines an ability of the person to perform the identified task further dependent on the information received from the user interface 120. The depicted embodiment thus enables a user of the system (such as the care giver or a medical practitioner, for example) to create, define, modify, alter information that may be used by the assessment unit 90. This can provide the flexibility to the many different contexts in which the system may operate.

It is also noted that the embodiment of FIG. 1 comprises first 140 and second 150 data stores. Here, the first data store 140 is a task complexity data store 140 that is adapted to store data relating to factors which influence required levels of functional ability to perform tasks. Accordingly, using information stored in the task complexity data store 140, the task complexity unit 70 can access data stored the task complexity data store 140 and obtain a task-specific complexity signal based on the accessed data.

The second data store 150 is an historical database 150 that is adapted to store data relating to determined abilities and/or tasks/activities of the person. The data of historical database can be accessed by the assessment unit 90 and then used when determining an ability of the person to perform the identified task. Thus, the assessment undertaken by the assessment unit 90 can be further based on historical information relating to one or more previously determined representations the person's functional ability. By using historical information, the accuracy and personalization of assessments may be improved.

Furthermore, the stored abilities and/or activities of the person may form a pattern that characterizes said person. Thus, pattern(s) of functional ability of a person may be stored in the historical database 150. Shifts in this pattern may indicate that the person is in need of help.

Deviations in the monitored abilities or tasks of a person may be used as an indicator of the well-being of the person. Therefore, in the embodiment of FIG. 1, the historical database 150 can be analyzed for irregularities or shifts in patterns. An irregularity in the database 150 may be detected, and an alert signal generated (by the assessment unit 90, for example) in response to the detected irregularity. Thus, according to embodiments, the assessment unit 90 is adapted to detect an irregularity in the historical database 150. An alert signal may be generated by the assessment unit 90 in response to an irregularity being detected. The irregularity may indicate that the person is in need of help for example. The alert signal may advise a medical practitioner, a caregiver, a family member or close relative to pay a visit to the monitored person. The alert signal can also be provided to the monitored person. For example, the alert signal may include a feedback signal advising the person to take a certain medication or preventative measures/action.

Figure 2:
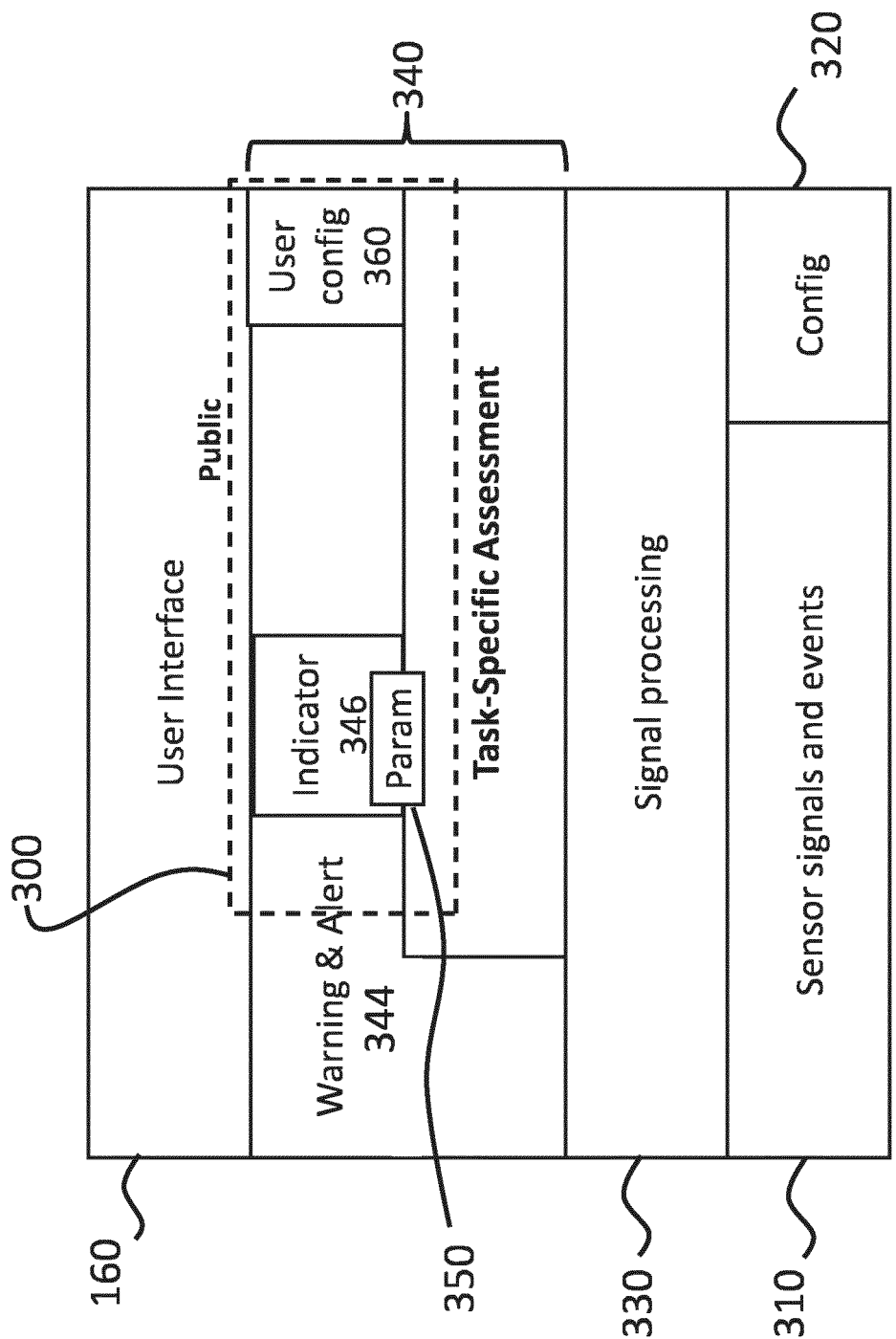
FIG. 2 is a layer diagram of the various layers of algorithms that together provide the data analytics to a system according to an embodiment.

Referring now to FIG. 2, there is depicted a layer diagram of the various layers of algorithms that together provide the data analytics to a system according to an embodiment. The algorithms are hosted on a (distributed) platform of which the encircled part 300, labelled "Public", is accessible to users of the system (using the user interface 120 for example).

At the lowest (i.e. bottom) layer, there is the system 310 of sensors (e.g. features 10,20,30 in FIG. 1) that issue signals, a continuous stream of data, and events, an irregular sequence of data. The data can be binary, e.g. open/close, or multi-valued, e.g. CO2 concentration. They can also be multi-dimensional as in the case of accelerometers. This layer ensures reliable transmission and storage of the data, including their time-stamping and synchronization. Missed or unreliable sensor data, in so far identified, are repaired when possible and otherwise indicated as such.

Also in the lowest (i.e. bottom) layer, the sensor configuration information 320 is also maintained. The configuration information 320 is instantiated upon installation of the system and maps the physical location of each sensor to its functional meaning.

Physical location includes aspects like the room, the furniture, and/or the appliance the sensors are attached to.

Functional meaning is the type of information the sensor provides to the algorithms, for example "drawer holding cutlery".

A single sensor may map to multiple functional meanings. For example, a sensor may be used to infer activity in Eating, Drinking or in Bathing. The floorplan or layout of the environment (e.g. building, ward, or house) is also stored in the configuration information 320. The floorplan/layout informs about matters like which rooms are adjacent (by doors), floor level, entrance door (can be front or back door, depending on user's habits) and other outdoors, and which functional rooms are physically collocated (for example, kitchen and dining room are a same physical space).

Directly above the lowest (i.e. bottom) layer, there are two layers of data processing: signal processing 330 and an (task-specific assessment) analytics layer 340. In the signal processing layer 330, data is cleaned, de-noised, quantized, and processed to extract features and to aggregate them into events. Preferably the data is processed to yield feature values that provide a more discriminative view on the data than the original raw data. Such processing will boost the classification and inference that is executed in the (task-specific assessment) analytics layer 340.

In the (task-specific assessment) analytics layer 340, there are at least three types of functions. The first concerns the identification or inference of tasks, the second the detection of anomalies 344 and risky situations that lead to Warnings & Alerts, and the third provides an Indicator function 346.

The assessment block 340 turns the sensor events into ADL events. In one embodiment, this function is largely based on simple decision-taking rules, but in other embodiments classification-based designs can be applied as they are known from the art of machine learning. Although the rules may appear simple from conceptual point of view, best implementation can still be through an imperative coding paradigm. This also warrants compatibility, and hence eases incorporation, of the classification-based designs. Still, for the interaction with user-provided inputs, the inferred tasks and/or functional ability values are output into a risk-based paradigm.

Preferably, an ADL event (fact) holds the following fields
1. ID—The ADL that is inferred.
2. TYPE—The type of the event, for the given ID (ADL).
3. SPACE—The physical location to which the event associates.
4. WHEN—The start moment in dd/mm/yyyy—hh:mm that the ADL (event) is detected.
5. DURATION—The duration in hh:mm the ADL is observed. If the event is instantaneous, the DUR is set to zero.
6. VALUE—The value of the event.

Figure 3:
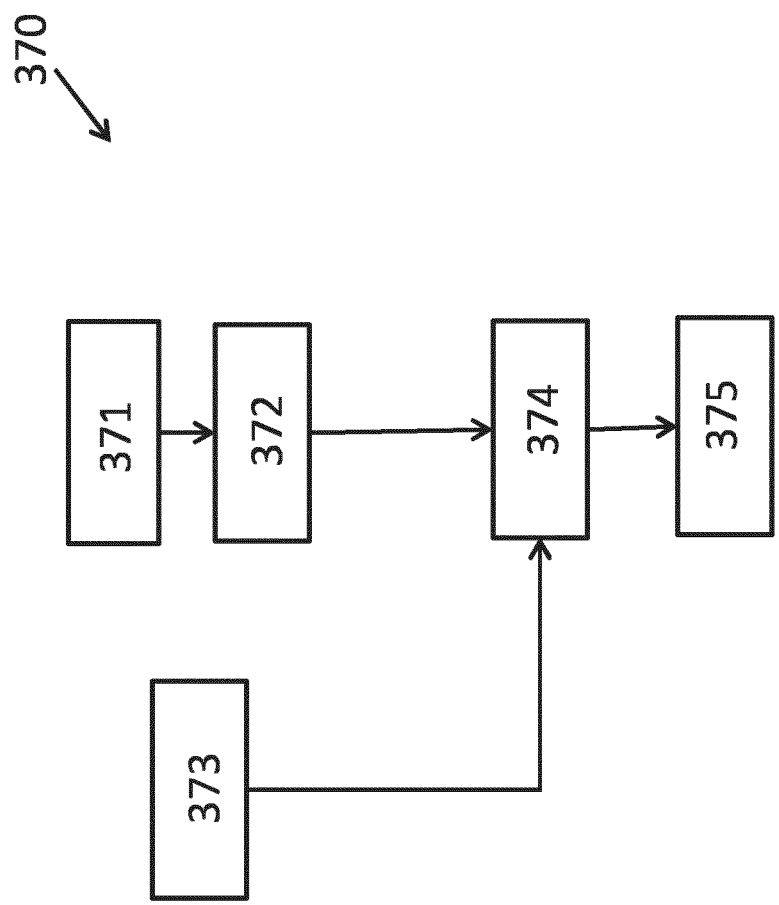
FIG. 3 is a flow diagram of a method for assessing the functional ability of a person to perform a task according to an embodiment.

Warning & Alerts are derived from either the processed sensor data, from the ADL events, or from the task-specific assessment. Thus, the Warning and Alerts layer extends across the whole of the assessment block 340 as depicted in FIG. 3.

An example algorithm to detect aberrations from the (processed) sensor data is as follows. In a first phase, the algorithm collects the sensor data and estimates the distribution in which they occur over the day. This can also be done offline, before installation, in which case the distributions represent the pattern is encountered in general, or encountered for the typical population to which the current elder belongs. The offline distribution can also be used to initiate the system. The obtained distributions serve as a reference. In the second phase, upon operation, the sensor data of the current day is collected and that pattern is tested against the reference pattern (distribution). Note that the reference distribution can be updated over time, by using the data of the recent days (and fading out those of earliest days, or from the initiation). A pattern can be considered as outlying if its probability (in terms of the reference distribution) is below a pre-defined (chosen) threshold.

The Indicator function is a signaling means that is used for presentation in the user interface, for example a dashboard displaying the different tasks and assessment as they have been detected and determined. An example indicator would be that the functional ability to perform a task is indicated. If they pass a given threshold (e.g. a level of functional ability required to perform a specific task), the task is presented in another way (other color, other size) in the UI.

The thresholds or task complexities can be set in the block labelled "Param" 350. The Indicator is fully implemented in the (public) rule system 300.

The block "Param" holds configurable parameters. The parameters are used by the rules in the rule system. The thresholds, as used by the Indicator function 346, constitute one set of parameters. Another set is formed by the parameters that are used in the aggregation part 342B. By changing the parameters, a user can modify the aggregation and indication of the data in the user interface 120 views.

The user config block 360 is another exemplary block. It allows a user to compose own their views of the ADL events or tasks as well as to set indicators on them. For example, a "bladder" view could be defined as the conglomerate of the ADLs Bed, Drinking, and Toilet. Thresholds can also be set through the user config block 360

The user interface 160 is the uppermost (i.e. top) layer, and uses techniques as are generally known in the art. It encompasses all views, including alert routes, to the appropriate stakeholders, as well as the controls to set parameters, such as the thresholds. It can read the data (facts) in the (public) rule system and can be called by the Warning & Alert function 344.

The user interface layer 160 also contains post-processing tasks, possibly modelled as a separate layer within the user interface layer 160. The post-processing tasks relate to computations that drive the presentation. For example, denoting a task as a Day or Night event is a function performed in this layer.

Referring now to FIG. 3, there is shown a flow diagram of a method 370 for assessing the functional ability of a person to perform a task according to an embodiment.

The method begins with the step 371 of identifying the task to be performed by the person. Here, in this example, sensor signals from various sensors situated on or near the person are received. The sensors signals are thus representative of one or more detected values of the person and/or the environment. Step 371 thus comprises processing the received sensor signals in accordance with various algorithms to identify (by calculation or inference) the task to be performed by the person.

Next, step 372, comprises obtaining a task-specific complexity signal representative of a required level of functional ability to perform the identified task. In particular, step 372 of this example, comprises querying a database to identify a predetermined required level of functional ability associated with the identified task. The database may thus comprise a relatively simple look-up table containing tasks and their associated required level of functional ability. In other embodiment, however, complex relationships and processing algorithms may be employed to determine or calculate a required level of functional ability based on the identified task and associated information.

In step 373, a functional ability signal representative of a determined functional ability of the person is obtained. More specifically, in this embodiment, the step 373 comprises receiving a sensor signal representative of a detected value of a property of the person. This sensor may therefore be a raw data signal which requires processing in accordance with an algorithm to identify (by calculation or inference) the functional ability of the person. Alternatively, the sensor signal may comprise a direct representation of the functional ability of the person, wherein the sensor has already calculated or determine the e functional ability of the person (for example, based on detected values and/or input information received from a person or separate system).

Also, for the avoidance of doubt, step 373 need not be performed after step 372. In other words, a functional ability signal representative of a determined functional ability of the person may be obtained separately or independently from the task-specific complexity signal.

Based on the both the obtained task-specific complexity signal and the obtained functional ability signal, an ability of the person to perform the identified task is determined in step 374. In this example, the determination simply comprises comparing information provided in the task-specific complexity signal (e.g. a numerical task complexity value representing a level of ability required to perform the task) with information provided in the functional ability signal (e.g. a numerical functional ability value) to determine if the ability of the person exceeds the ability required to perform the task. Put another way, the task-specific complexity signal defines a task-specific threshold value that the functional ability of the person is compared against. If the threshold is exceeded, for example, it is determined that the person is able to perform the identified task independently (e.g. without assistance from a caregiver).

Also, modified versions of the proposed method may further take account of historical information relating previously determined value of the person's functional ability when determining the ability of the person to perform the identified task. Use of such historical information may improve the accuracy and personalization of the determination step 374.

Finally, in step 375, assessment signal representative of the determined ability of the person to perform the identified task is generated. In this example, the assessment signal simply comprises a Boolean value indicating whether or not the person has the required ability to perform the identified task.

The proposed method therefore generates an assessment signal from two types of information. The first type of information relates to the identified task, whereas the second type of information relates to the functional ability of the person. Thus, inferred tasks or ADLs may be used to generate an assessment signal which is dependent on the inferred tasks or ADLs. In this way, use of inferred tasks or ADLs may enable the creation of simple warnings and alerts. Raw or processed (e.g. sampled, cleaned, time-stamped, etc.) sensor data/signals may be used to generate an assessment signal dependent on the sensor data/signals directly. The sensor data/signals may therefore enable the creation of task-specific and/or accurate warnings and alerts.

Also, by way of example of a modification to the step 374 of determining an ability of the person to perform the identified task, a task-specific risk signal representative of a risk of the identified task may be obtained and used in the determination of an ability of the person to perform the identified task. The task-specific risk signal may, for example comprise information relating to the person's perceived risk of the identified task and a caregiver's perceived risk of the identified task. In this way, perceived risks associated with the identified task may be taken account of when determining an ability of the person to perform the identified task. A task having a higher perceived risk may, for example, impact the determination step so that a required functional ability is increased (e.g. a threshold level used to assess whether a person should be allowed to perform the task may be modified according to the perceived risk).

Thus, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

Figure 4:
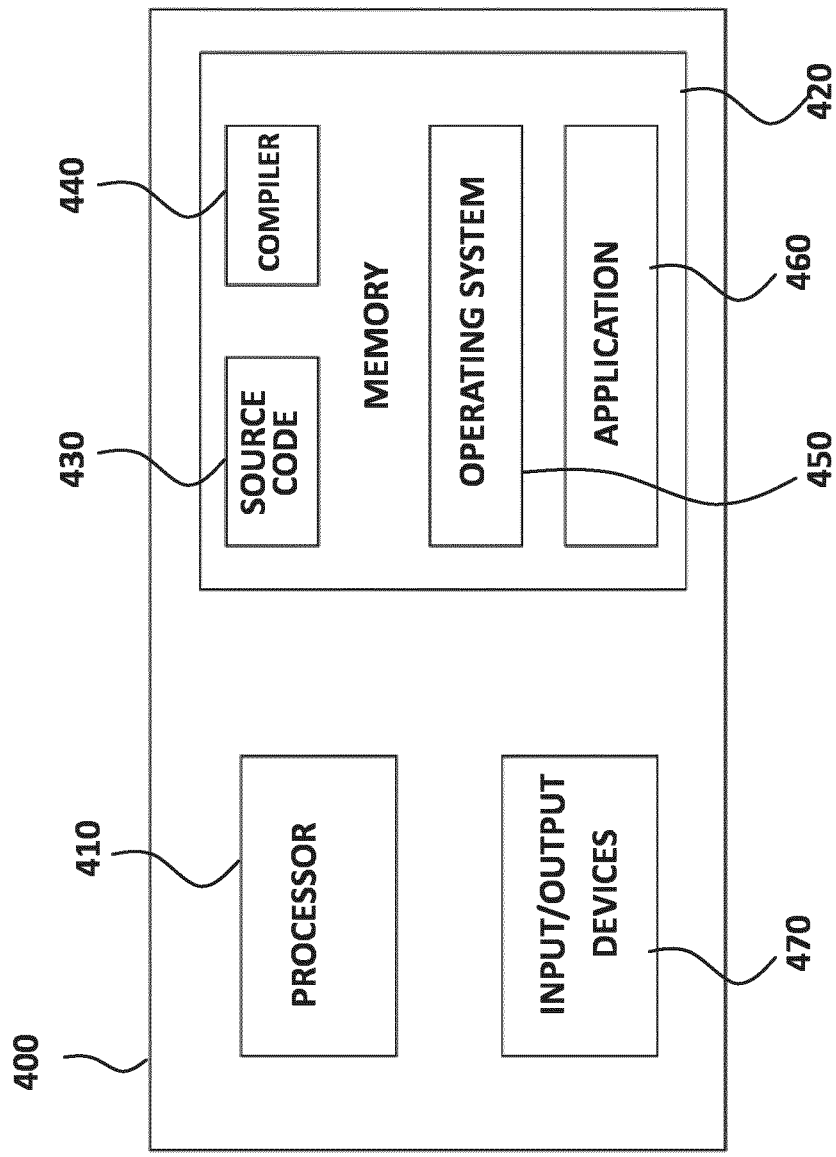
FIG. 4 is a simplified block diagram of a computer within which one or more parts of an embodiment may be employed.

FIG. 4 illustrates an example of a computer 400 within which one or more parts of an embodiment may be employed. Various operations discussed above may utilize the capabilities of the computer 400. For example, one or more parts of a system for assessing the functional ability of a person to perform a task may be incorporated in any element, module, application, and/or component discussed herein.

The computer 400 includes, but is not limited to, PCs, workstations, laptops, PDAs, palm devices, servers, storages, and the like. Generally, in terms of hardware architecture, the computer 400 may include one or more processors 410, memory 420, and one or more I/O devices 470 (such as environmental sensors, infection source sensors, user susceptibility sensors, etc.) that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a digital signal processor (DSP), or an auxiliary processor among several processors associated with the computer 400, and the processor 410 may be a semiconductor based microprocessor (in the form of a microchip) or a microprocessor.

The memory 420 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the memory 420 may include one or more separate programs, each of which comprises an ordered listing of executable instructions for implementing logical functions. The software in the memory 420 includes a suitable operating system (O/S) 450, compiler 440, source code 430, and one or more applications 460 in accordance with exemplary embodiments. As illustrated, the application 460 comprises numerous functional components for implementing the features and operations of the exemplary embodiments. The application 460 of the computer 400 may represent various applications, computational units, logic, functional units, processes, operations, virtual entities, and/or modules in accordance with exemplary embodiments, but the application 460 is not meant to be a limitation.

The operating system 450 controls the execution of other computer programs, and provides scheduling, input-output control, file and data management, memory management, and communication control and related services. It is contemplated by the inventors that the application 460 for implementing exemplary embodiments may be applicable on all commercially available operating systems.

Application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, FORTRAN, COBOL, Perl, Java, ADA, .NET, and the like.

The I/O devices 470 may include input devices such as, for example but not limited to, a mouse, keyboard, scanner, microphone, camera, etc. Furthermore, the I/O devices 470 may also include output devices, for example but not limited to a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or intranet.

If the computer 400 is a PC, workstation, intelligent device or the like, the software in the memory 420 may further include a basic input output system (BIOS) (omitted for simplicity). The BIOS is a set of essential software routines that initialize and test hardware at startup, start the O/S 450, and support the transfer of data among the hardware devices. The BIOS is stored in some type of read-only-memory, such as ROM, PROM, EPROM, EEPROM or the like, so that the BIOS can be executed when the computer 400 is activated.

When the computer 400 is in operation, the processor 410 is configured to execute software stored within the memory 420, to communicate data to and from the memory 420, and to generally control operations of the computer 400 pursuant to the software. The application 460 and the O/S 450 are read, in whole or in part, by the processor 410, perhaps buffered within the processor 410, and then executed.

When the application 460 is implemented in software it should be noted that the application 460 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 460 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Thus, there is proposed a concept for providing guidance about a person's functional ability in relation to a specific task of activity, wherein the unique attributes of the user and/or the task are taken into account. By taking account of a required level of functional ability to perform an identified task, an assessment of the person's ability to perform the task may be determined. Also, proposed embodiments may take account of the risk(s) (as perceived by the person/patient and/or a caregiver, for example) as an additional factor for determining a risk associated with the person attempting undertake the task.

At this point, it is noted that the above described embodiments are merely example embodiments and that several extensions thereto and/or variations may be made.

For example, several types of wearable assessment or monitoring devices can be envisaged, including glasses, pendants, smartwatches, clip-on devices, smart textiles etc. Also, embodiments may be integrated with a calendar to assist in planning of activities based on obtained assessments.

Also, proposed systems may be combined with data on location-specific activities to assist determination of a person's functional ability to perform an identified task.

Data from the system may be combined with personal data on health and well-being to generate a personal profile of "safe" and "risky" activities, locations and interactions. Data may also be transmitted for the benefit of other peer users or patients, and such data could serve as input to task/activity avoidance map software.

Other suitable extensions and variations to the above disclosed embodiments will be apparent to the skilled person.

For example, embodiments may be adapted to implement flexible thresholds that can be adapted according to user and/or with respect to time. In this way, it may be possible to have more or less strict versions of algorithms used to create alerts or notifications. For instance, embodiments may be arranged to vary thresholds from "strict" where perceived risks are elevated to "normal" and through to "light" if perceived risks are low.

A preferred implementation may be to only inform the user when a certain assessment is achieved. This may help to ensure a seamless solution without inhibiting social interaction.

The proposed concept has the advantage that a network of sensors and portable computing devices with monitoring and/or communication functions can be easily transformed into an assessment system.

Aspects of the present invention may be embodied as a monitoring method or system at least partially embodied by a portable computing device or distributed over separate entities including a portable computing device. Aspects of the present invention may take the form of a computer program product embodied in one or more computer-readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor 110 may be written in any combination of one or more programming languages, including an object oriented programming language such as Java, Smalltalk, C++ or the like and conventional procedural programming languages, such as the "C" programming language or similar programming languages. The program code may execute entirely on the processor 110 as a stand-alone software package, e.g. an app, or may be executed partly on the processor 110 and partly on a remote server. In the latter scenario, the remote server may be connected to the head-mountable computing device 100 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the data processor 110 of the cardiopulmonary resuscitation coordination system including portable computing device, such that the instructions create means for implementing the functions/acts specified in the flowchart and/or block diagram block or blocks. These computer program instructions may also be stored in a computer-readable medium that can direct the cardiopulmonary resuscitation guidance system including the portable computing device to function in a particular manner.

The computer program instructions may, for example, be loaded onto the portable computing device to cause a series of operational steps to be performed on the portable computing device and/or the server, to produce a computer-implemented process such that the instructions which execute on the portable computing device and/or the server provide processes for implementing the functions/acts specified in the flowchart and/or block diagram block or blocks. The computer program product may form part of a patient monitoring system including a portable computing device.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A system comprising:
  a sensor configured to generate one or more sensor signals; and
  a processor adapted to receive the one or more sensor signals, and further adapted to:
    identify a task to be performed by a person based on said received one or more sensor signals;
    obtain a task-specific complexity signal representative of a required level of functional ability to perform the identified task;
    obtain a functional ability signal representative of a determined functional ability of the person;
    obtain a task-specific risk signal representative of a risk of the identified task, wherein the task-specific risk signal comprises information related to both the person's perceived risk of the identified task, and a caregiver's perceived risk of the identified task;
    determine an ability of the person to perform the identified task based on the task-specific complexity signal, the task-specific risk signal and the determined functional ability signal; and
    generate an assessment signal representative of the determined ability of the person to perform the identified task.

2. The system according to claim 1, wherein the task-specific risk signal further comprises information relating to an availability of the caregiver.

3. The system according to claim 1, wherein the one or more sensor signals are representative of a detected value of a property of at least one of: the person; and an environment.

4. The system according to claim 3, further comprising a sensor adapted to: (i) detect a value of a property of at least one of: the person, and the environment, and (ii) to generate a sensor signal representative of the detected value.

5. The system according to claim 1, further comprising a task complexity data store adapted to store data relating to factors that influence required levels of functional ability to perform tasks, and wherein the processor is adapted to access data stored in the task complexity data store and to obtain the task-specific complexity signal from the accessed data.

6. The system according to claim 1, wherein the processor is further adapted to determine the ability of the person to perform the identified task based on historical information relating to one or more previously determined representations of the person's functional ability.

7. The system according to claim 1, further comprising an input interface adapted to receive an input for defining or modifying at least one of: the task to be performed by the person, the required level of functional ability to perform the identified task, the functional ability of the person, the risk of the identified task, and data relating to factors that influence required levels of functional ability to perform tasks.

8. The system according to claim 1, wherein the system is adapted to provide the generated assessment signal to at least one of: the person, a medical practitioner, and a caregiver.

9. The system according to claim 1, further adapted to store the generated assessment signal in a database.

10. The system according to claim 1, wherein the task to be performed is taken from a group comprising: eating, cooking, medicating, sleeping, toileting, bathing, and washing.

11. A method, comprising:
  generating, by each of one or more sensors of a task identification system, a sensor signal;
  receiving, by a processor of the task identification system, the generated sensor signal from each of the one or more sensors;
  identifying a task to be performed by a person based on the received generated sensor signal;
  obtaining a task-specific complexity signal representative of a required level of functional ability to perform the identified task;
  obtaining a functional ability signal representative of a determined functional ability of the person;
  obtaining a task-specific risk signal representative of a risk of the identified task, wherein the task-specific risk signal comprises information related to both the person's perceived risk of the identified task, and a caregiver's perceived risk of the identified task;
  determining an ability of the person to perform the identified task based on the task-specific complexity signal, the task-specific risk signal and the determined functional ability signal; and
  generating an assessment signal representative of the determined ability of the person to perform the identified task.

12. A non-transitory computer-readable storage medium of a task identification system, the non-transitory computer-readable storage medium configured to store instructions that, when executed by a processor of the task identification system, perform the steps of:
  receiving a sensor signal generated by each of one or more sensors of the task identification system;
  identifying a task to be performed by a person based on the received generated sensor signal;
  obtaining a task-specific complexity signal representative of a required level of functional ability to perform the identified task;
  obtaining a functional ability signal representative of a determined functional ability of the person;

obtaining a task-specific risk signal representative of a risk of the identified task, wherein the task-specific risk signal comprises information related to both the person's perceived risk of the identified task, and a caregiver's perceived risk of the identified task;

determining an ability of the person to perform the identified task based on the task-specific complexity signal, the task-specific risk signal and the determined functional ability signal; and generating an assessment signal representative of the determined ability of the person to perform the identified task.

* * * * *